United States Patent
Nossal et al.

(10) Patent No.: US 10,565,351 B2
(45) Date of Patent: Feb. 18, 2020

(54) ANALYSIS AND RULE GENERATION OF MEDICAL DOCUMENTS

(71) Applicant: 3M INNOVATIVE PROPERTIES COMPANY, St. Paul, MN (US)

(72) Inventors: Michael A. Nossal, Seattle, WA (US); Guoli Wang, North Potomac, MD (US)

(73) Assignee: 3M Innovative Properties Company, Saint Paul, MN (US)

( * ) Notice: Subject to any disclaimer, the term of this patent is extended or adjusted under 35 U.S.C. 154(b) by 784 days.

(21) Appl. No.: 15/242,670

(22) Filed: Aug. 22, 2016

(65) Prior Publication Data
US 2017/0061085 A1    Mar. 2, 2017

Related U.S. Application Data

(60) Provisional application No. 62/208,925, filed on Aug. 24, 2015.

(51) Int. Cl.
G06F 19/00       (2018.01)
G16H 10/60       (2018.01)

(52) U.S. Cl.
CPC .......... G06F 19/328 (2013.01); G16H 10/60 (2018.01)

(58) Field of Classification Search
CPC ...... G06F 19/328; G06F 17/271; G16H 10/60
See application file for complete search history.

(56) References Cited

U.S. PATENT DOCUMENTS

| | | | | |
|---|---|---|---|---|
| 5,768,423 A * | 6/1998 | Aref | ................... | G06K 9/00879 |
| | | | | 382/228 |
| 8,346,804 B2 | 1/2013 | Phillips | | |
| 8,615,530 B1 * | 12/2013 | LeTourneau | ............ | G06F 17/10 |
| | | | | 707/797 |
| 2010/0185685 A1 * | 7/2010 | Chew | .................... | G06F 16/334 |
| | | | | 707/803 |
| 2010/0286979 A1 * | 11/2010 | Zangvil | ................. | G06F 17/273 |
| | | | | 704/9 |
| 2014/0372458 A1 * | 12/2014 | Jurca | ................... | G06F 16/9024 |
| | | | | 707/754 |

(Continued)

OTHER PUBLICATIONS

Aditya Vanka, Skip Trie Matching for Real-Time OCR Output Error Corrrection on Smartphones, 2013, Utah State University, all pages. (Year: 2013).*

(Continued)

*Primary Examiner* — Jay A Morrison
*Assistant Examiner* — Antonio J Caiado
(74) *Attorney, Agent, or Firm* — 3M Innovative Properties Company; Jonathan V. Sry

(57) ABSTRACT

This disclosure describes a computerized system for managing medical information, the system including at least one computing device configured to receive a plurality of medical documents, determine skip grams comprising tokens for the plurality of medical documents, wherein each of the skip grams comprises one or more tokens of at least one of the medical documents, and populate a trie data structure based on the skip grams. The at least one computing device is further configured to prune the plurality of nodes of the trie based on one or more criteria to produce a pruned trie of nodes, determine rules for associating medical billing codes with the skip grams of the pruned trie of nodes based on pointwise mutual information, and output the determined rules.

21 Claims, 7 Drawing Sheets

(56) References Cited

U.S. PATENT DOCUMENTS

| | | | | |
|---|---|---|---|---|
| 2015/0066991 A1* | 3/2015 | Goyal | ............... | G06F 16/90344 |
| | | | | 707/798 |
| 2016/0170982 A1* | 6/2016 | Djuric | ................... | G06F 16/353 |
| | | | | 707/740 |
| 2016/0210423 A1* | 7/2016 | Tanner, Jr. | ............ | G06F 19/328 |
| 2017/0011309 A1* | 1/2017 | Tsutaoka | ................ | G06N 20/00 |
| 2017/0351821 A1* | 12/2017 | Tanner, Jr. | ............. | G16H 30/20 |
| 2019/0005049 A1* | 1/2019 | Mittal | ................. | G06F 17/2705 |

OTHER PUBLICATIONS

Lazaridou, "Combining Language and Vision with a Multimodal Skip-gram Model," Center for Mind/Brain Sciences, University of Trento, Jan. 13, 2015, 10 pages.

* cited by examiner

ANALYSIS AND RULE GENERATION OF MEDICAL DOCUMENTS

TECHNICAL FIELD

This disclosure relates to systems and techniques for managing medical information contained in medical documents.

BACKGROUND

In the medical field, accurate processing of records relating to patient visits to hospitals and clinics ensures that the records contain reliable and up-to-date information for future reference. Accurate processing may also be useful for medical systems and professionals to receive prompt and precise reimbursements from insurers and other payors. Some medical systems may include electronic health record (EHR) technology that assists in ensuring records of patient visits and files are accurate in identifying information needed for reimbursement purposes. These EHR systems generally have multiple specific interfaces into which medical professionals across different healthcare facilities and settings may input information about the patients and their visits.

SUMMARY

In general, this disclosure describes systems and techniques for efficiently analyzing medical document data that are annotated with medical billing codes to determine rules for associating billing codes with medical documents based on the presence of certain identifiers. A computing system configured in this disclosure uses an algorithm that examines "skip grams" of tokens from medical documents and builds a "trie" data structure (also referred to as a prefix tree) comprised of the skip grams. Based on the nodes of the trie, the computing system may determine rules for associating medical billing codes with medical documents that include the set of tokens defined by one of the rules.

More particularly, a computing system configured in accordance with the techniques of this disclosure builds the trie data structure by adding nodes comprising skip grams one layer at a time. The computing system then analyzes and prunes the nodes. During the pruning process, the computing system examines and removes nodes from the trie in order to reduce the search space and memory consumption associated with the nodes. After pruning, the executing computing device examines nodes from a current level of the tree that were not pruned for possible output as rules that associate a billing code with a skip gram comprising a set of tokens.

In one example, this disclosure describes a computer-implemented method for managing medical information performed by one or more processors of at least one computing device, the method including receiving, by the one or more processors, a plurality of medical documents; determining, by the one or more processors, skip grams comprising tokens for the plurality of medical documents, wherein each of the skip grams comprises one or more tokens of at least one of the medical documents, and populating, by the one or more processors, a trie data structure based on the skip grams. Populating the trie includes: adding a null root node to the trie, and adding a plurality of nodes to the trie. The plurality of nodes each have a parent node including either: the root node or another one of the plurality of nodes, and each of the plurality of nodes comprises one of the determined skip grams. For every one of the plurality of nodes having a respective parent node, a skip gram of the one of the plurality of nodes has a greater size than a skip gram of the parent node of the one of the plurality of nodes. The method further includes pruning, by the one or more processors, the plurality of nodes of the trie based on one or more criteria to produce a pruned trie of nodes, determining, by the one or more processors, rules for associating medical billing codes with the skip grams of the pruned trie of nodes based on pointwise mutual information, and outputting, by the one or more processors, the determined rules.

In another example, this disclosure describes a computerized system for managing medical information, the system including one or more processors of at least one computing device, wherein the one or more processors are configured to receive a plurality of medical documents, determine skip grams comprising tokens for the plurality of medical documents, wherein each of the skip grams comprises one or more tokens of at least one of the medical documents, and populate a trie data structure based on the skip grams. To populate the trie, the at least one computing device is further configured to: add a null root node to the trie, and add a plurality of nodes to the trie, wherein the plurality of nodes each have a parent node comprising either: the root node or another one of the plurality of nodes. Each of the plurality of nodes includes one of the determined skip grams, wherein, for every one of the plurality of nodes having a respective parent node, a skip gram of the one of the plurality of nodes has a greater size than a skip gram of the parent node of the one of the plurality of nodes. The one or more processors are further configured to: prune the plurality of nodes of the trie based on one or more criteria to produce a pruned trie of nodes, determine rules for associating medical billing codes with the skip grams of the pruned trie of nodes based on pointwise mutual information, and output the determined rules.

In an additional example, this disclosure describes a non-transitory computer-readable storage medium including instructions that, when executed, cause one or more processors to receive a plurality of medical documents, determine skip grams comprising tokens for the plurality of medical documents, wherein each of the skip grams comprises one or more tokens of at least one of the medical documents, and populate a trie data structure based on the skip grams. The instructions that cause the at least one processor to populate the trie further include instructions that cause the at least one processor to: add a null root node to the trie, and add a plurality of nodes to the trie, wherein the plurality of nodes each have a parent node comprising either: the root node or another one of the plurality of nodes. Additionally, each of the plurality of nodes comprises one of the determined skip grams, wherein, for every one of the plurality of nodes having a respective parent node, a skip gram of the one of the plurality of nodes has a greater size than a skip gram of the parent node of the one of the plurality of nodes. Additionally, the non-transitory computer-readable storage medium further includes instructions that cause the one or more processors to: prune the plurality of nodes of the trie based on one or more criteria to produce a pruned trie of nodes, determine rules for associating medical billing codes with the skip grams of the pruned trie of nodes based on pointwise mutual information, and output the determined rules.

The details of one or more examples of the described systems, devices, and techniques are set forth in the accompanying drawings and the description below. Other features,

DETAILED DESCRIPTION

Figure 1:
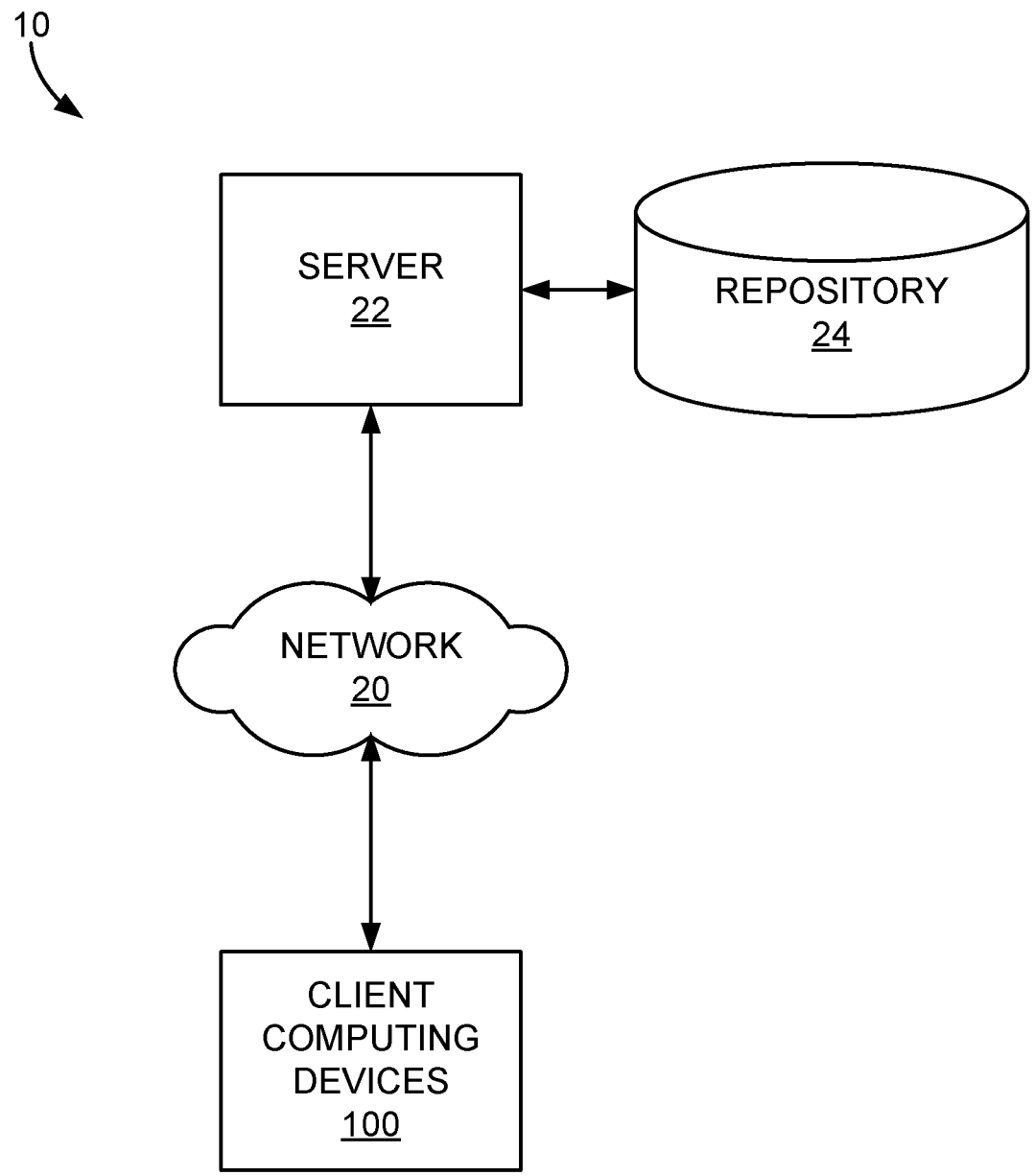
FIG. 1 is a block diagram illustrating an example computing system configured to determine, and/or apply rules for associating billing codes with a medical document consistent with this disclosure.

This disclosure describes systems and techniques for analyzing medical documents to determine rules for associating billing codes with medical documents based on tokens in the medical documents. When a physician visits with a patient (e.g., a patient encounter), the physician may perform various tasks such as evaluating the patient, reviewing medical history of the patient, and determining the current medical condition of the patient. The physician may also, or alternatively, perform a medical procedure on the patient during the patient encounter that may be related to the medical condition. The physician (or other medical professional such as a physician's assistant or nurse) typically uses a computerized medical record system to enter information (e.g., into a medical document) documenting aspects of the patient encounter as medical information related to the patient.

Hospitals and healthcare companies may utilize medical coders to manually associate billing codes with services rendered. The process of manually associating billing codes with medical documents is time consuming and may be error-prone. A computing system, referred to as an automated coding system (ACS) may receive and analyze medical documents to automatically determine rules for associating medical codes with medical documents. By applying the determined rules, an automated coding system may be able to automatically associate billing codes with medical documents, which may save significant amounts of manual labor, time, and money.

As described herein, a computing system configured in accordance with the techniques of this disclosure may parse medical documents into words and/or non-space characters data of medical documents referred to herein as "tokens." In the example sentence, "the quick brown fox jumps over the lazy dog," each word of the sentence comprises a token. Non-dictionary words, sequences of numbers, and non-alphanumeric characters (e.g., "# xzy123") may also comprise tokens. In some examples, non-dictionary word tokens may be associated with medical billing codes.

Computing devices (e.g., a networked server or stand-alone computing devices) described herein may receive medical documents, and parse the medical documents into tokens. The medical documents may include one or more characters combined in one or more words, one or more phrases, sentences, paragraphs, any combination thereof within an EHR (electronic health record).

The computing system may analyze the tokens of medical documents to generate skip-grams. A skip-gram is a particular way of modeling language. A skip-gram is based on a construct referred to as an n-gram. An n-gram is a consecutive subsequence of length n of some sequence of tokens $w_1 \ldots w_n$. A k-skip-n-gram is a length-n subsequence having components that occur at distance at most k from each other. As an example, for the phrase "the quick brown fox jumps over the lazy dog," the set of all 1-skip-2 grams comprises: "the brown," "quick fox," "brown jumps," "fox over," "jumps the," "over lazy," and the dog," as well as all the 2-grams (also referred to as bigrams), e.g., "the quick," "quick brown," etc. Skip grams may be more useful relative to n-grams for analyzing word data due to the data sparsity associated with n-grams.

Using skip grams to model language may results in additional overhead relative to using n-grams, however. For example, when searching text using skip-grams, the search space may be very large. As an example, a skip-gram of size 4 with window size 6, the 10 word sentence "the quick brown fox jumped over the lazy dog's back" would yield 6 windows, each of which has 6!/2! permutations of size of 4, yielding 2160 skip grams.

The search space for skip grams increases dramatically when analyzing multiple documents with larger amounts of words. As an example, if a computing system were to determine every skip gram of the above example having a size 4 with window size 6 for each of 1,000,000 documents, and each document consists of 100 ten-word sentences, there would be roughly 200 billion skip grams. The search space would be further increased if the computing system attempted to consider that each skip-gram could be associated with several billing codes. Such a large number of skip grams would easily overwhelm an exhaustive skip-gram search algorithm even if that algorithm were configured to run on multiple computers using a distributed framework. To reduce the search space, the techniques of this disclosure modify the word window that is used to roughly model local dependencies between words, and to signify co-reference. The techniques of this disclosure attempt to construct word models that are more precise than models that treat entire documents as a bag of unrelated words. In some examples, the techniques may be specifically designed with rules that may improve the processing of passages in medical documents.

To address the rapid growth of memory associated with analyzing such a large body of words and documents, a computing system configured in accordance with the techniques of this disclosure iteratively builds, prunes, and analyzes a prefix tree data structure (referred to as a "trie") to determine rules for associating medical codes with medical documents as will be described in greater detail below.

A trie is traditionally a tree data structure comprising a set of nodes in which each node of the tree represents a string. The path from a leaf node to the root of the tree represents the co-occurrence set of strings. The trie has a null root node (i.e. a node having a null string as its value). The techniques of this disclosure modify the traditional trie such that 1) each node is associated with a skip gram and 2) each additional level of depth within the trie corresponds to an increase, in size of 1increments, the skip grams at that level of the trie relative to the skip grams at the previous (parent) depth level of the trie. So, the first level of the trie includes nodes comprising skip grams of size 1 (unigrams), the second level of the trie includes nodes comprising skip grams of size 2 (bigrams), and so on.

The computing system operating in accordance with this disclosure iteratively adds levels of depth to the trie. That is, the computing device adds skip gram nodes to the current depth. As will be described in greater detail below, if a skip gram cannot be a child node of any of the nodes at the depth level above the current depth level, then the computing system does not add this skip gram to the trie.

After the computing system adds a layer of nodes to the current depth level of the trie, the computing system prunes (i.e. removes) nodes from the trie that do not meet one or more criteria. Pruning may be based on one or more criteria such as a threshold count for the histogram of each code (e.g., a code may be dropped from a node if the count of a node's histogram is below a threshold number or the node may be removed from the trie of the count is zero) or a number of enterprises associated with each node (e.g., a node associated with fewer enterprises such as only a single hospital, the node may be the result of a template at that enterprise and less useful than a node from multiple enterprises). Pruning nodes reduces the search space associated with the trie, as well as the memory consumption of the trie. Reducing the memory consumption and search space may improve performance, especially for a single "master" computing device of the computing system. The master computing device may need to maintain the entire trie in system memory while the prefix tree is being populated.

After populating a level of the trie with nodes, the computing system then examines the remaining nodes for potential output as rules. As an example, the computing system may output a node as a rule if a probability of that rule exceeds a specified output threshold probability. The outputted rule may consist of the skip gram set of features (e.g., a feature set for the skip gram) that map to a specified billing code. The set of features or feature set of a skip gram may include one or more combinations of tokens that may be available from the skip gram.

Once the computing system outputs any rules, the computing system generates one or more bloom filters corresponding to the nodes of the trie. The bloom filter is similar to a hashing function, and is a memory-efficient way that a computing device can use to determine whether an element is a member of a set of elements. A bloom filter cannot definitively indicate whether an item is a member of a set. However, a bloom filter can definitively indicate whether an item is not a member of a set.

After generating bloom filters for the current depth level of the trie, the computing system begins populating the next level of the trie, and determines, using the bloom filters generated for the previous level of the trie, whether a candidate skip gram node for addition to the trie is a potential member of any of the existing skip gram sets of the trie. If the candidate node, to be added, is potentially a member of at least one of the existing sets of skip grams, the computing system adds the node comprising the candidate skip gram to the next level of the trie. If the computing system determines that the candidate node is not a member of any skip gram nodes of the previous depth level, the computing system prunes the candidate skip gram node, and does not add the node to the trie. The computing system continues iteratively pruning skip gram nodes, outputting rules, and adding layers to the trie until all skip grams having the maximum skip gram window size have been analyzed and either added or pruned.

In some examples, if applying a medical code using an outputted medical coding rule has a probability that exceeds a certain probability threshold, a computing system consistent with this disclosure may automatically apply the rule to a medical document, i.e. may automatically apply the medical code associated with the rule to the medical document. In some examples, if an outputted medical coding rule does not have a probability that exceeds the threshold, there may be a risk that automatically associating a medical code with a medical document may be erroneous. Thus in the cases where the probability does not exceed the threshold, the computing system may indicate and/or a medical coder may still manually review medical documents to which coding rules and their associated medical codes have been automatically applied.

FIG. 1 is a block diagram illustrating an example computing system configured to determine, and/or apply rules for associating billing codes with a medical document consistent with this disclosure. As described herein, computing system 10 may include one or more client computing devices 100, a network 20, server computing device 22, and repository 24. Server computing device 22 may retrieve medical documents from repository 24. Client computing devices 100 may be configured to communicate with server 22 via network 20.

In some examples, server computing device 22 and client computing devices 100 may be configured to perform the techniques described herein using a distributed framework, for example the Apache Spark™ distributed computing framework. Server computing device 22 may be configured as a Spark master node, and client computing devices 100 may be configured as worker nodes. More generally, server computing device 22 may be responsible for providing data to client computing devices 100, and for aggregating results returned from client computing devices 100.

Server 22 may be and/or include one or more computing devices connected to client computing devices 100 via network 20. Server 22 may perform the techniques described herein, and a user may interact with system 10 via client computing devices 100. Network 20 may include a proprietary or non-proprietary network for packet-based communication. In one example, network 20 may include the Internet, in which case each of client computing devices 100 and server 22 may include communication interfaces for communicating data according to transmission control protocol/internet protocol (TCP/IP), user datagram protocol (UDP), or other communication protocol. More generally, however, network 20 may include any type of communication network, and may support wired communication, wireless communication, fiber optic communication, satellite communication, or any type of techniques for transferring data between two or more computing devices (e.g., server 22 and client computing devices 100).

Figure 2:
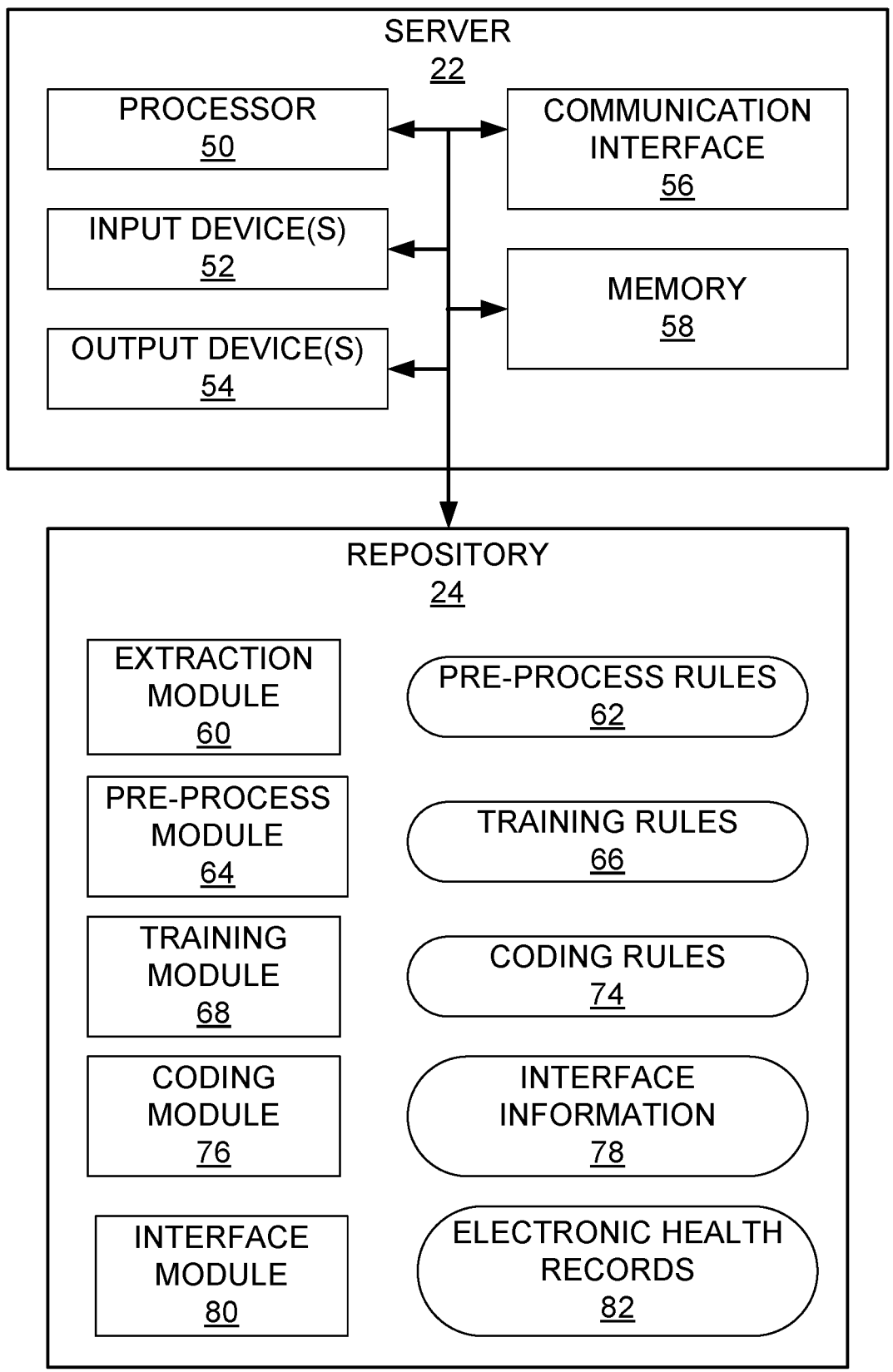
FIG. 2 is a block diagram illustrating the server and repository of the example distributed system of FIG. 1.

Server 22 may include one or more processors, storage devices, input and output devices, and communication interfaces, as described in FIG. 2. Server 22 may be configured to provide a service to one or more clients, such an Apache Spark™ distributed computing service, MapReduce distributed computing service, or other parallel and/or distributed computing services. Server 22 may operate within a local network or be hosted in a Cloud computing environment.

Client computing devices 100 may be a computing device associated with an entity (e.g., a hospital, clinic, university, or other healthcare organization) that provides information to a physician during a patient encounter and/or receives input documenting aspects of the patient encounter. Examples of client computing device 100 include personal computing devices, computers, servers, mobile devices, smart phones, and tablet computing devices. Client computing devices 100 may comprise one or more Apache Spark™ worker nodes. Client computing devices 100 may be configured to receive medical document data generated by server 22 and stored in repository 24. Server 22 may also be configured to communicate with multiple client computing devices 100 associated with the same entity and/or different entities.

When a physician sees a patient in either an outpatient clinic or during an office visit (e.g., a patient encounter), the physician typically performs an evaluation of the patient, the patient's medical history and/or the patient's current medical condition. The physician may also perform a medical procedure on the patient during the patient encounter or prescribe treatment related to the patient's medical condition. The physician (or other medical professional) may record information related to the patient and the patient encounter in a medical document. A device, such as one of client computing devices 100 may allow, via the medical documentation software, the physician to generate medical documents related the patient in repository 24. These previously generated medical documents may be stored by client computing devices 100 and/or repository 24, and retrieved for viewing and/or selection by the physician.

As described herein, system 10 may operate to generate rules for associating medical codes with medical documents. System 10 may generate rules in real-time or after a medical document has been completed and stored in the EHR. In this manner, system 10 may automate and improve the speed and/or accuracy of medical coding, which may further improve billing and other medical practices.

In one example, system 10 may include one or more computing devices (e.g., server 22) configured to receive one or more medical documents related to respective patient encounters with one or more physicians. System 10 may store these medical documents in repository 24 for later use and/or incorporation in the EHR for the patient. Server 22 may also retrieve these previously generated medical documents for display to physicians at a later time via client computing devices 100. During or after a patient encounter, client computing devices 100 may receive user input generating a medical document describing aspects of the patient encounter. Medical documents related to the patient encounter may include a natural language representing the patient encounter as created by the physician. For example, the physician may dictate or type various background information, observations, diagnoses, procedures performed, or any other notes regarding the patient encounter. Dictated or narrated information may include voice data recognized and converted to text for processing via NLP techniques described herein. As the new medical document is saved by client computing devices 100, client computing devices 100 may transmit the new medical document to server 22 via network 20. Server 22 may store the new medical document in repository 24.

Client computing devices 100 may be used by a user (e.g., a medical professional such as physician, a healthcare facility administrator, a governmental regulatory agency, or a medical coding expert) to generate medical documents as described herein. Client computing devices 100 may also comprise an Apache Spark™ worker node in various examples. Client computing devices 100 may include one or more processors, memories, input and output devices, communication interfaces for interfacing with network 20, and any other components that may facilitate the processes described herein. In some examples, client computing devices 100 may be similar to computing device 100 of FIG. 3. In this manner, computing system 10 comprising server computing device 22 and client computing devices 100 may be configured to, with the aid of server 22, receive a plurality of medical documents, determine skip grams comprising tokens for the plurality of medical documents, wherein each of the skip grams comprises one or more tokens of at least one of the medical documents, and populate a trie data structure based on the skip grams. To populate the trie, server device 22 and/or client devices 100 may be further configured to: add a null root node to the trie, and add a plurality of nodes to the trie, wherein the plurality of nodes each have a parent node comprising either: the root node or another one of the plurality of nodes. Each of the plurality of nodes comprises one of the determined skip grams, wherein, for every one of the plurality of nodes having a respective parent node, a skip gram of the one of the plurality of nodes has a greater size than a skip gram of the parent node of the one of the plurality of nodes. Server device 22 and/or client devices 100 may be further configured to: prune the plurality of nodes of the trie based on one or more criteria to produce a pruned trie of nodes, determine rules for associating medical billing codes with the skip grams of the pruned trie of nodes based on pointwise mutual information, and output the determined rules in some examples.

FIG. 2 is a block diagram illustrating the server and repository of the example system 10 of FIG. 1. As shown in FIG. 2, server 22 includes processor 50, one or more input devices 52, one or more output devices 54, communication interface 56, and memory 58. Server computing device 22 may be a computing device configured to perform various tasks and interface with other devices, such as repository 24 and client computing devices (e.g., client computing devices 100 of FIG. 1). Although repository 24 is shown external to server 22, server 22 may include repository 24 within a server housing in other examples. Server 22 may also include other components and modules related to the processes described herein and/or other processes. The illustrated components are shown as one example, but other examples may be consistent with various aspects described herein.

Processor 50 may include one or more general-purpose microprocessors, specially designed processors, application specific integrated circuits (ASIC), field programmable gate arrays (FPGA), a collection of discrete logic, and/or any type of processing device capable of executing the techniques described herein. In some examples, processor 50 or any other processors herein may be described as a computing device. In one example, memory 58 may be configured to store program instructions (e.g., software instructions) that are executed by processor 50 to carry out the processes described herein. Processor 50 may also be configured to execute instructions stored by repository 24. Both memory 58 and repository 24 may be one or more storage devices. In other examples, the techniques described herein may be executed by specifically programmed circuitry of processor 50. Processor 50 may thus be configured to execute the techniques described herein. Processor 50, or any other processors herein, may include one or more processors.

Memory 58 may be configured to store information within server 22 during operation. Memory 58 may comprise a computer-readable storage medium. In some examples, memory 58 is a temporary memory, meaning that a primary purpose of memory 58 is not long-term storage. Memory 58, in some examples, may comprise a volatile memory, meaning that memory 58 does not maintain stored contents when the computer is turned off. Examples of volatile memories include random access memories (RAM), dynamic random access memories (DRAM), static random access memories (SRAM), and other forms of volatile memories known in the art. In some examples, memory 58 is used to store program instructions for execution by processor 50. Memory 58, in one example, is used by software or applications running on server 22 (e.g., one or more of modules 60, 64, 68, 76, and 80) to temporarily store information during program execution.

Input devices 52 may include one or more devices configured to accept user input and transform the user input into one or more electronic signals indicative of the received input. For example, input devices 52 may include one or more presence-sensitive devices (e.g., as part of a presence-sensitive screen), keypads, keyboards, pointing devices, joysticks, buttons, keys, motion detection sensors, cameras, microphones, touchscreens, or any other such devices. Input devices 52 may allow the user to provide input via a user interface.

Output devices 54 may include one or more devices configured to output information to a user or other device. For example, output device 54 may include a display screen for presenting visual information to a user that may or may not be a part of a presence-sensitive display. In other examples, output device 54 may include one or more different types of devices for presenting information to a user. Output devices 54 may include any number of visual devices (e.g., display devices, lights, or other device with visual output), audible devices (e.g., one or more speakers), and/or tactile feedback devices. In some examples, output devices 54 may represent both a display screen (e.g., a liquid crystal display or light emitting diode display) and a printer (e.g., a printing device or module for outputting instructions to a printing device). Processor 50 may present a user interface via one or more of input devices 52 and output devices 54, whereas a user may control the generation and analysis of medical documents via the user interface. In some examples, the user interface generated and provided by server 22 may be output for display by a client computing device (e.g., one or more of client computing devices 100).

Server 22 may utilize communication interface 56 to communicate with external devices via one or more networks, such as network 20 in FIG. 1, or other storage devices such as additional repositories over a network or direct connection. Communication interface 56 may be a network interface card, such as an Ethernet card, an optical transceiver, a radio frequency transceiver, or any other type of device that can send and receive information. Other examples of such communication interfaces may include Bluetooth, 3G, 4G, and WiFi radios in mobile computing devices as well as USB. In some examples, server 22 utilizes communication interface 56 to wirelessly communicate with external devices (e.g., client computing devices 100) such as a mobile computing device, mobile phone, workstation, server, or other networked computing device. As described herein, communication interface 56 may be configured to receive medical documents, and/or instructions from a user, as instructed by processor 50.

Repository 24 may include one or more memories, repositories, databases, hard disks or other permanent storage, or any other data storage devices. Repository 24 may be included in, or described as, cloud storage. In other words, information stored in repository 24 and/or instructions that embody the techniques described herein may be stored in one or more locations in the cloud (e.g., one or more repositories 24). Server 22 may access the cloud and retrieve or transmit data as requested by an authorized user, such as client computing devices 100. In some examples, repository 24 may include Relational Database Management System (RDBMS) software. In one example, repository 24 may be a relational database and accessed using a Structured Query Language (SQL) interface that is well known in the art. Repository 24 may alternatively be stored on a separate networked computing device and be accessed by server 22 through a network interface or system bus, as shown in the example of FIG. 2. Repository 24 may in other examples be an Object Database Management System (ODBMS), Online Analytical Processing (OLAP) database or other suitable data management system.

Repository 24 may store instructions and/or modules that may be used to perform the techniques described herein related to generating rules for associating medical codes with medical documents. As shown in the example of FIG. 2, repository 24 includes extraction module 60, pre-process module 64, training module 68, coding module 76, and interface module 80. Processor 50 may execute each of modules 60, 64, 68, 76, and 80 as needed to perform various tasks. Repository 24 may also include additional data such as information related to the function of each module and server 22. For example, repository 24 may include pre-process rules 62, training rules 66, coding rules 74, interface information 78, and electronic health records 82. Repository 24 may also include additional data related to the processes described herein. In other examples, memory 58 or a different storage device of server 22 may store one or more of the modules or information stored in repository 24. In some examples, one or more of modules 60, 64, 68, 76, and 80 and/or associated instructions may be stored in a different memory such as memory 58 of server 22, a remote storage device, or a memory of another computing device.

As described herein, server 22 may receive medical information entered (e.g., created) by a physician or at the direction of a physician to represent an encounter with a patient. For example, processor 50 may receive one or more medical documents describing the patient encounter or including notes regarding the patient. These medical documents may be stored in Electronic Health Records (EHR) 82. EHR 82 may include medical documents for a single patient or medical documents for a plurality of respective patients. EHR 82 may include training medical documents, which server computing device 22 may use to generate rules for associating medical codes with medical documents.

Processor 50 may be configured to analyze the text of medical documents 82 using skip grams to generate a trie data structure. Server computing device 22 may analyze the trie data structure to generate rules (e.g., coding rules 74) for associating medical codes with medical document data. Processor 50 may receive medical documents 82 from an entity such as a healthcare organization and/or receive the medical documents already stored in EHR 82. In some examples, extraction module 60 may first identify and extract the sections from each of the training medical documents. For example, extraction module 60 may extract sections based on formatting breaks in the text of each medical document, such as headings location within the medical documents. In some examples, extraction module 60 may extract sections according to breaks identified by annotations for the respective training medical documents. In some examples, extraction module 60 may extract sections based on input received from a user through the interface module 80. In order to improve the efficiency of representing electronic health records 82, extraction module 60 may convert each word of all of electronic health records 82 to unique integer representations corresponding to each unique word.

Pre-process module 64 may then perform pre-processing on each of the extracted sections of the training medical documents according to the instructions stored in pre-process rules 62 in various examples. For example, pre-process rules 62 may cause pre-processing module 64 to remove stop words (e.g., prepositions and connector words such as he, is, at, which, and on), remove words that occur less than a predetermined number of times within the section (e.g., less than two times or less than three times), and/or ignore any lines less than a predetermined number of characters long (e.g., less than 5 characters or less than 10 characters). These modifications to the sections of text may aid in the natural language processing used to generate the classification model. In addition pre-process module 64 may mask all numbers in the text of each section into hash tags or other anonymous characters or symbols. This masking of numbers may promote patient privacy.

Training module 68 may generate, based on the pre-processed sections of the training medical documents according to the instructions in training rules 66, one or more tries and skip grams that model the training medical documents and used for coding other medical documents. Training rules 66 may include a set of instructions (e.g., what type of classifier to use, which sections of training documents to use, identify any annotations important to the training processes, sizes and window sizes for skip grams, pruning rules, or any other relevant information) that training module 68 may use to model the training medical documents for future medical coding. For example, training module 68 may be configured to train a statistical machine learning classifier with the pre-processed sections of the training medical documents.

Training module 68 may perform techniques described herein such as generating skip grams and populating one or more tries based on the skip grams. Training module 68 may also prune nodes within the one or more tries. As discussed herein, pruning may remove less important nodes of the trie such that only more common, or predictively important, nodes remain in the trie for association with respective medical billing codes. Training module 68 may also generate bloom filters for respective nodes of each trie. In this manner, training module 68 may also generate rules for associating medical billing codes with one or more pruned tries, and, in some examples, generate rules for selecting medical billing codes for medical documents in EHRs. Training module 68 may generate the rules fully automatically based on each trie and the available medical codes. Alternatively, a coding professional may at least partially assist the coding rule generation by manually reviewing the nodes of each trie. These rules may be stored as coding rules 74 and used by a coding module 76 to select medical billing codes appropriate to represent the concepts contained within a medical document.

In some examples, the training medical documents may be analyzed by a statistical machine learning classifier operating within the training module 68 to identify natural language associated with various types of medical information that is suitable for automated medical coding. An example statistical machine learning classifier may be a Naïve Bayes classifier, but a different probabilistic classifier may be used in other examples. In some examples, training module 68 may include a natural language processing (NLP) engine that can process one or more of the training medical documents and select a statistical machine learning classifier most appropriate for the information contained in the training medical documents. The training medical documents may be of different types of medical documents. Training module 68 may select different statistical machine learning classifiers for respective different types of medical documents.

In some examples, before determining skip grams and tries for the training medical documents, server 22 may utilize extraction module 60 to extract sections of text from the medical documents that may not be relevant to the medical coding process. This extraction may reduce the search space for the skip grams and/or mask private data of the patient. In this manner, processor 50 may execute extraction module 60 and/or pre-process module 64 for those training medical documents used to generate the skip grams and tries described herein.

Coding rules 74 may include instructions that define the operation of coding module 76. For example, coding rules 74 may define the operation of one or more coding engines applied by coding module 76. Each coding engine may be specific to a particular medical codeset (e.g., IDC-9 or ICD-10 codesets) and/or specific to a particular type of medical information. For example, coding module 76 may be configured to operate a diagnosis coding engine, a procedural coding engine, a historical coding engine, and an evaluation management coding engine. Each of these coding engines may correspond to the types of information contained within a section of text as identified by the codability indicia. Although coding module 76 may operate different coding engines, separate coding modules may operate respective coding engines in other examples. Coding module 76 may output the medical codes generated for each of the processed sections of text. In accordance with the techniques of this disclosure, coding rules 74 may comprise a set of skip grams that are mapped to one or more associated medical codes.

Interface module 80 may output any of the information generated by modules 60, 64, 68, and 76. For example, interface module 80 may output the one or more tries generated by training module 68 to another computing device for use in generating coding rules and/or coding other medical documents or for display at a computing device (e.g., client computing devices 100). Interface module 80 may also output the criteria used to prune the tries, eliminated nodes during pruning, or any other information related to the process of generating skip grams and the one or more tries. In addition, interface module 80 may be configured to output generated medical codes to other computing devices or for display. Interface module 80 may also be configured to receive information from other computing devices, such as training medical documents or other medical documents to be processed. Interface information 78 may include instructions that define the operation of interface module 80. Interface module 80 may also receive user input requesting various modules to perform the functions described herein.

Figure 3:
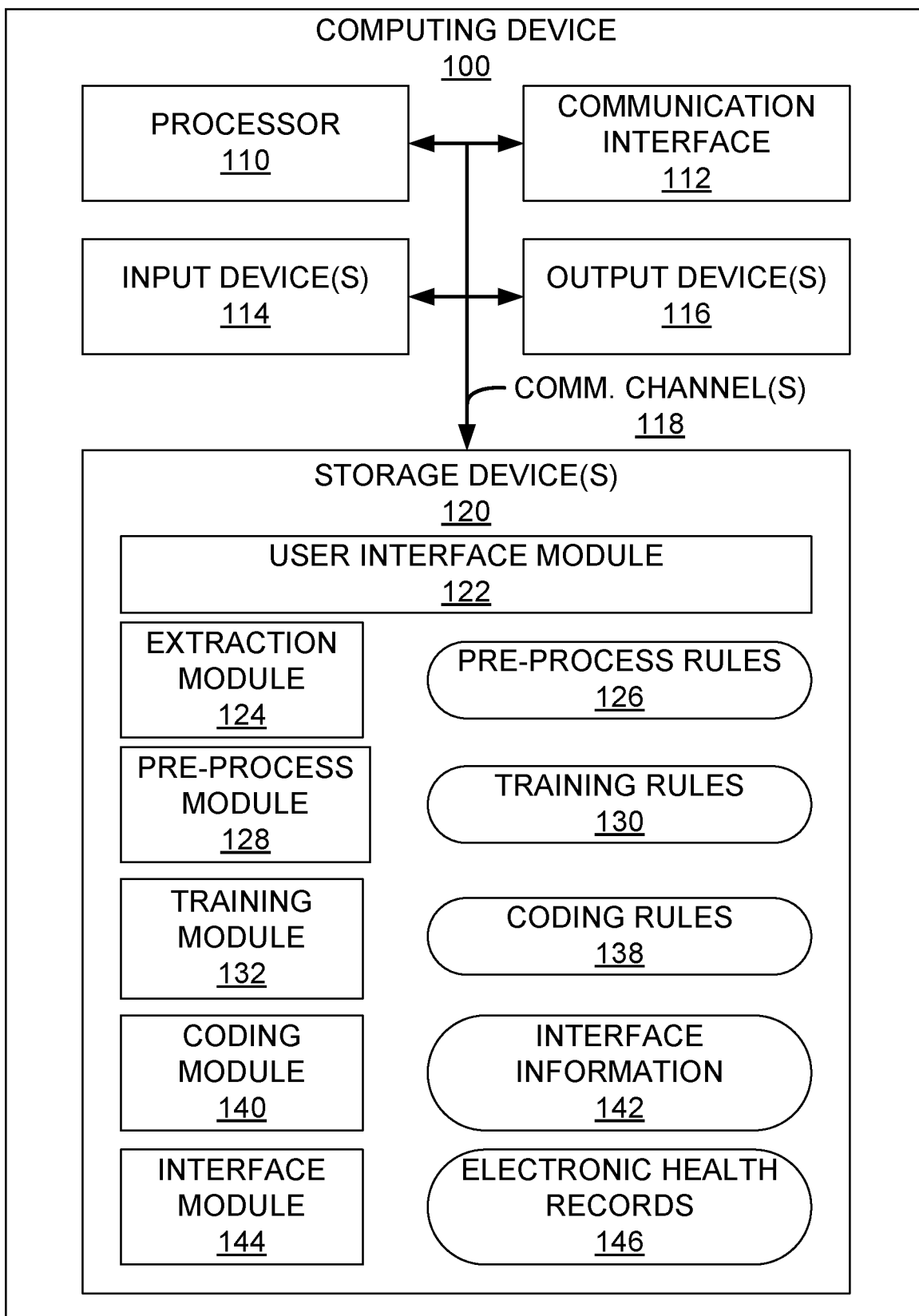
FIG. 3 is a block diagram illustrating a stand-alone computing device configured to determine and/or apply rules for associating billing codes with a medical document consistent with this disclosure.

FIG. 3 is a block diagram illustrating client computing device 100 configured to determine and/or apply rules for associating billing codes with a medical document consistent with this disclosure. Client computing device 100 may be substantially similar to server 22 and repository 24 of FIG. 2. However, client computing device 100 may be a stand-alone computing device configured to analyze medical documents to populate a trie data structure and output medical coding rules. Computing device 100 may be configured as a workstation, desktop computing device, notebook computer, tablet computer, mobile computing device, or any other suitable computing device or collection of computing devices.

As shown in FIG. 3, computing device 100 may include processor 110, one or more input devices 114, one or more output devices 116, communication interface 112, and one or more storage devices 120, similar to the components of server computing device 22 of FIG. 2. Computing device 100 may also include communication channels 118 (e.g., a system bus) that allows data flow between two or more components of computing device 100, such as between processor 110 and storage devices 120. In various examples, computing device 100 may comprise a node of a distributed computing system, for example an Apache Spark™ worker node. More generally, client computing device 100 may receive and process data from server computing device 22. Computing device 100 also includes one or more storage devices 120, such as a memory, that stores information such as instructions for performing the processes described herein of generating rules for associating medical codes with medical documents by populating a prefix trie comprising skip gram nodes, pruning the layers of the prefix trie, generating rules for associating medical codes with medical documents, and outputting the generated rules.

Storage devices 120 may include data for one or more modules and information related to the codability indicia and automatic medical coding described herein. For example, storage devices 120 may include extraction module 124, pre-process module 128, training module 132, coding module 140, and interface module 144, similar to the modules described with respect to repository 24 of FIG. 2. Storage devices 120 may also include information such as pre-processing rules 126, training rules 130, coding rules 138, interface information 142, and Electronic Health Records (EHR) 146, similar to the information described as stored in repository 24.

The information and modules of storage devices 120 of computing device 100 may be specific to a healthcare entity that employs computing device 100 to generate rules for associating medical codes with medical documents, and to apply the rules to determine medical codes associated with the medical documents. For example, coding module 140 may analyze medical documents of electronic health records 146 to determine rules for associating medical codes with medical documents. In any case, computing device 100 may be configured to perform any of the processes and tasks described herein and with respect to server 22 and repository 24. Storage devices 120 may also include user interface module 144, which may provide a user interface for a user via input devices 114 and output devices 116.

In some examples, input devices 114 may include one or more scanners or other devices configured to convert paper documents into electronic clinical documents that can be processed by computing device 100. In other examples, communication interface 112 may receive electronic clinical documents from a repository or individual clinician device on which clinical documentation are initially generated. Communication interface 112 may thus send and receive information via a private or public network.

Figure 4A:
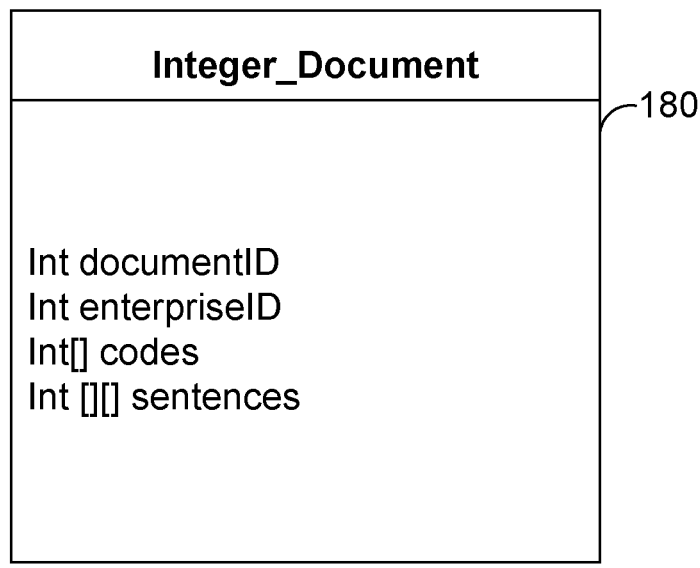
FIG. 4A is a conceptual diagram illustrating a class diagram of an integer-mapped document class.

FIG. 4A is a conceptual diagram illustrating a class diagram of an integer-mapped document class. Before populating a trie data structure with skip gram nodes, server computing device 22 and client devices 100 map the tokens of medical documents from alphanumeric strings to unique integer values. Class diagram 180 of FIG. 4A illustrates that the devices of computing system 10 may be used to represent an integer-mapped document. In various examples, server device 22 and/or client devices 100 may represent the classes discussed above with respect to FIGS. 4A and 4B (e.g., Integer_Documents and Trie_Node) using native collections backed by arrays rather than by standard collection libraries that are autoboxed (e.g., in Java).

The "Integer_Document" class comprises the following members: "documentID," "enterpriseID," "codes," and "sentences." In various examples, the documentID member may comprise a unique integer identifier associated with a document. The enterpriseID may comprise an integer identifier of an enterprise, such as a hospital, healthcare organization or other healthcare entity. The "codes" member may comprise an integer array of billing codes that are associated with the current document, and the sentences member may comprise a two-dimensional integer array. The "sentences" integer array may be indexed by sentence number, and each sentence may comprise a set of integer-mapped strings as described above.

To generate an integer-mapped document, extraction module 60 and/or pre-process module 64 of server computing device 22 and/or client device 100 may detect sentence boundaries and may populate the members of an Integer_Document based on the processed sentence data, as well as other data from a non-integer mapped document.

Figure 4B:
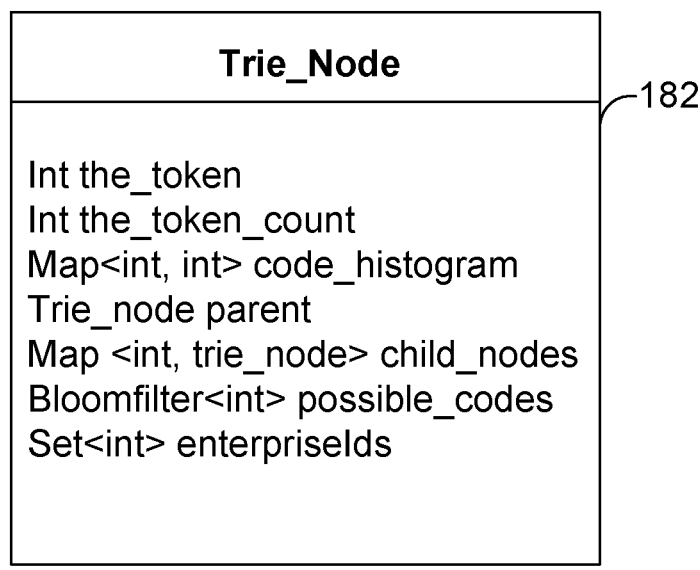
FIG. 4B is a conceptual diagram illustrating a class diagram of a trie node class.

FIG. 4B is a conceptual diagram illustrating a class diagram of a trie node class. As described elsewhere, server computing device 22 and client devices 100 generate a trie data structure. The trie is comprised of layers of nodes, which further comprise skip grams. Class diagram 182 illustrates the members of a "Trie_Node" class, which represents a node of the trie. The trie_node class may comprise at least the following members: "the token" "the token_count," "code_histogram," "parent," "child_nodes," "possible_codes," and "enterpriseIds."

The token and token_count members may both comprise integer values of the trie_node class. The value of the token indicates an integer-mapped token of a skip gram corresponding to that node. The "the token_count" member indicates the number of times that a particular word within the skip gram occurs. The code_histogram member represents a histogram that may comprise a map of integer values to integer values, or the cumulative total of the count data members (e.g., the total number of times that the token occurs. The key of the code_histogram map may be an integer-mapped string, and the values of the map may indicate a total number of times that the particular value (e.g., a token) occurs within the histogram.

The child_nodes data member may comprise a map that represents the child nodes of the current node. The key values of the child_nodes member may comprise integer values, and the values of the map comprise trie_node data structures. For a particular key value, the child_nodes member returns a particular child trie_node based on the key value, which is an integer-mapped token.

The bloomfilter data member represents a bloom filter data structure that is indexed by an integer key value. The bloom filter data structure indicates whether an integer-mapped word of a skip gram is already a member of the trie_node associated with the bloom filter. The enterpriseIds data member may comprise a set data structure comprised of integer values. Each value of the enterpriseIds set may indicate a particular enterprise (e.g., clinic, hospital, healthcare organization, or another enterprise entity) associated with that particular document.

Figure 5:
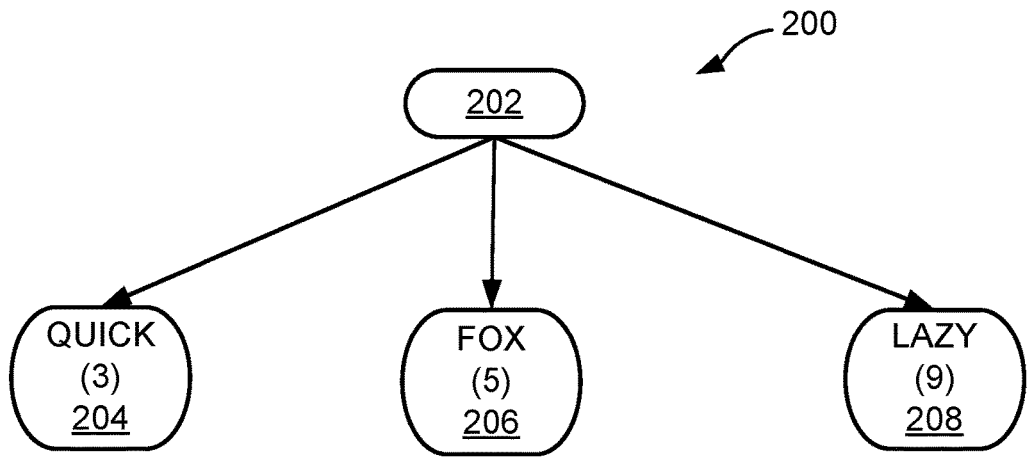
FIG. 5 is a conceptual diagram of an example trie data structure comprising skip gram nodes in accordance with the techniques of this disclosure.
Figure 6:
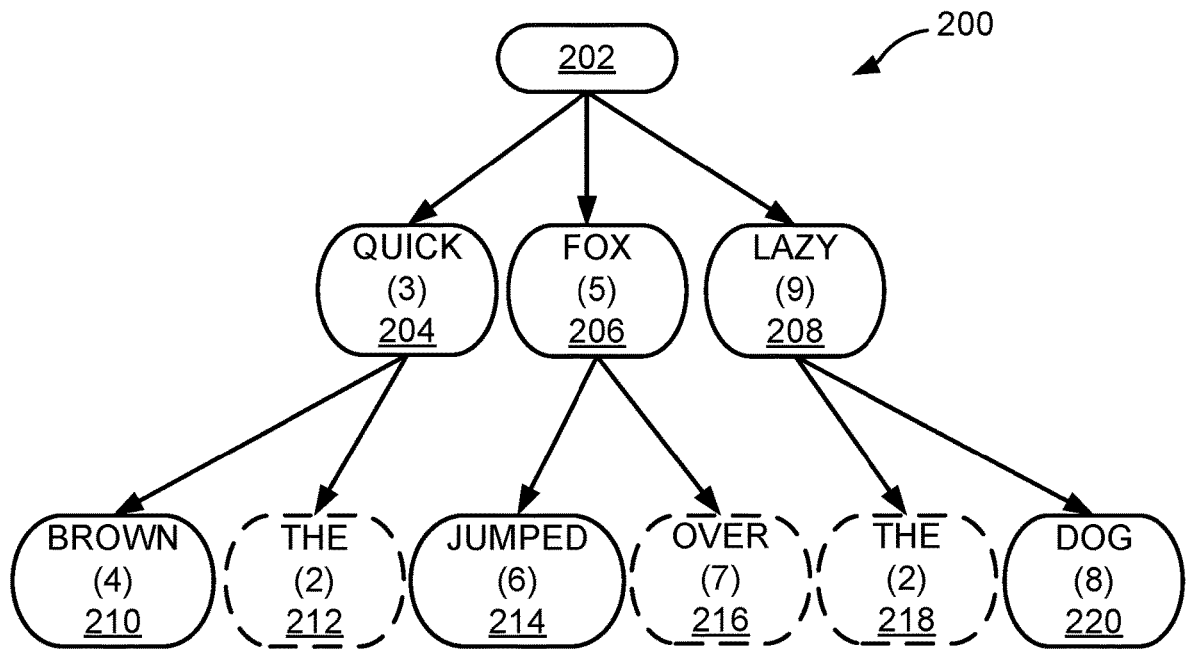
FIG. 6 is a conceptual diagram of an example trie data structure comprising nodes in accordance with the techniques of this disclosure.
Figure 7:
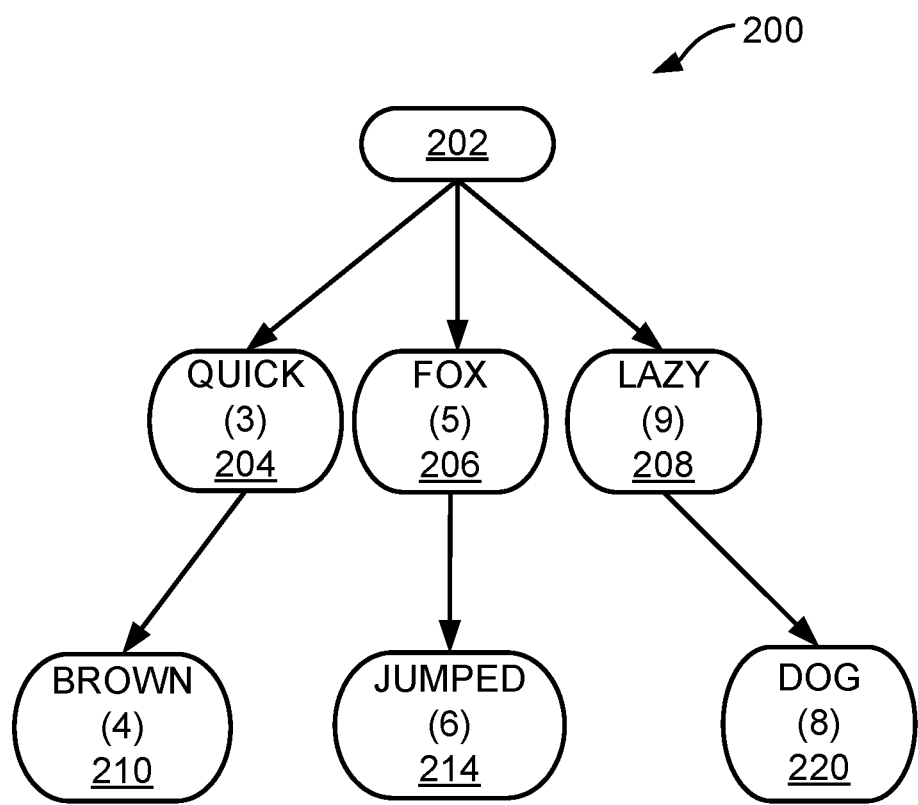
FIG. 7 is a conceptual diagram illustrating an example refined trie data structure after performing pruning.

FIG. 5 is a conceptual diagram of a trie data structure 200 comprising skip gram nodes in accordance with the techniques of this disclosure. Trie 200 comprises a set of nodes further comprising root node 202, first layer nodes 204, 206, and 208. In the example of FIG. 4A, server computing device 22 and/or client computing devices 100 examine a hypothetical medical document which includes the phrase: "the quick brown fox jumped over the lazy dog." It should be understood that server computing device 22 and client computing devices 100 operate on a plurality of medical documents each containing numerous words, but that only the aforementioned phrase is illustrated in FIGS. 5, 6, and 7 for the purpose of simplicity. Based on the aforementioned phrase, server computing device 22 and client computing devices 100 construct trie 200.

Generally speaking, before a trie, such as trie 200 is populated, server computing device 22 and/or client devices 100 generate a histogram of all the tokens and from all retrieved medical documents. To reduce the memory consumption, i.e. so as not to have to store each entire token from each medical document in memory, server computing device 22 and client devices 100 map each of the tokens (e.g., codes and text) of the medical documents to integer values. Representing the tokens of a document using integer values reduces memory consumption relative to using string representations of the tokens.

Server computing device 22, client devices 100, and/or or another computing device may generate a Spark Resilient Distributed Dataset (RDD) based on the integer-mapped medical documents. Once the RDD has been generated, server computing device 22 and client computing devices 100 may iteratively execute various sequence and combination functions on the Spark Resilient Distributed Dataset (RDD) of documents to generate layers of trie 200, as well as to generate any associated output rules. To begin the process of populating the trie, server computing device 22 may invoke a function of the Spark application programming interface (API) as follows:

docs.aggregate(beginning_trie)(sequence_operationOp, combination_operatation).

In the above method call, "docs" is an object comprising an RDD of integer-mapped medical documents (e.g., the Integer_Document class described above with respect to FIG. 4A). The docs object includes the aggregate method as a class member.

The aggregate method has a first "zeroValue" argument, a second "seqOp," argument, and a third "combOp" argument. The argument "beginning_trie" corresponds to the zeroValue argument, and represents a beginning state of the trie (e.g., trie 200) before server computing device 22 or client computing devices 100 add layers to the trie, e.g. a null root node. "Sequence_operationOp," is a function that corresponds to the seqOp argument. The sequence_operationOp is a function that aggregates items. In this this example, the items to be aggregated in sequence_operationOp comprise the trie and the RDD item type, which further comprise integer-mapped medical documents.

Server device 22 and/or client devices 100 further map the integer-mapped medical documents to an "addDocument" method of the trie. AddDocument may receive an argument indicating a maximum skip gram size (i.e. a maximum number of words that a skip gram may span). When executed, the addDocument method generates the skip gram permutations of the specified level of the trie. Server device 22 and/or client devices 100 lookup each of these permutations in the trie and update the trie as additional skip grams are added to the trie.

If a parent node for a specified skip gram exists in the trie, server device 22 or one of client devices 100 creates a child node corresponding to the specified skip gram if the child node does not exist. If no parent node exists, then server device 22 or one of client devices 100 previously pruned the node. Consequently, server device 22 and/or client devices 100 do not update the trie for this skip gram. If server device 22 or client devices 100 determine that the node corresponding to a particular skip gram exists in the current level of the trie, or if the node is generated, then server device 22 and/or client devices 100 update the count and histograms associated with the node.

The combination_operation argument is a function that takes two tries as arguments, and returns a single trie that represents the merging of the two tries passed as arguments. Because server device 22 and/or client devices 100 add nodes one level at a time, only nodes from the current level are examined as part of the combination_operation function. If a corresponding node from the first trie exists in the other trie, then server device 22 and/or client devices 100 update its count and code histogram are updated. If the node does not exist, then server device 22 and/or client devices 100 add the node as a child node to the node corresponding to the parent node in the second trie argument.

Each of the above methods runs on computing system 10 further comprising server computing device 22 and client devices 100. More particularly, server device 22 and/or client devices 100 may each execute any of the above functions or methods, and may return an updated trie structure as a result of executing the above functions.

At startup of the rule determination and trie population process, server computing device 22 and client devices 100 generate a histogram of all the tokens and codes from all the supplied documents (e.g., Integer_Documents). A parameter, referred to as "min_count," specifies the minimum number of times a token needs to occur for the token not to be pruned. Server computing device 22 and client devices 100 remove tokens from consideration that occur fewer times than this supplied parameter (e.g., 3 times) from the documents, as well as tokens that occur very frequently (e.g., tokens that occur in greater than 50% of documents).

In the example of FIG. 5, server computing device 22 and client devices 100 have populated trie 200 with first layer nodes 204, 206, and 208. In order to conserve memory, server computing device 22 and client computing devices 100 have mapped the words of each medical document to a unique integer value. The integer-mapped document comprises at least part of an RDD. For the purposes of example, the phrase "the quick brown fox jumped over the lazy dog," both instances of the word "the" would be represented by the same integer value, e.g. "2."

In trie 200, first layer nodes 204, 206, and 208 comprise unigram nodes, i.e. nodes that represent a skip gram of length one. First layer node 204 comprises the skip gram "quick," and is mapped to an integer value of 3. Node 206 comprises the skip gram "fox," and is mapped to the integer value 5, and node 208 comprises skip gram "lazy," is mapped to the integer value 9.

After nodes 204, 206, and 208 are added to trie 200, Server computing device 22 and client computing devices 100 generate the values of the bloom filter class members for each node of trie 200 (i.e. nodes 204, 206, and 208) before the next layer of nodes can be added to trie 200. The bloom filters are not illustrated for the sake of simplicity. Server computing device 22 and client devices 100 can use the bloom filters to determine whether a skip gram is definitely not a member (i.e. cannot be a child of) a parent node.

After server computing device 22 and client devices 100 have added nodes 204, 206, and 208 to the first layer of trie 200, server computing device 22 and client devices 100 increase the size of the skip grams by one, (i.e. from a size of one to a size of two), and determine whether to add the skip grams of size two to trie 200. The process of determining whether to add the second layer nodes to trie 200 is illustrated in FIG. 6.

FIG. 6 is a conceptual diagram of a trie data structure 200 comprising skip gram nodes in accordance with the techniques of this disclosure. In FIG. 6, server computing device 22 and client devices 100 determine whether to add skip grams corresponding nodes 210, 212, 214, 216, 218, and 220 to trie 200. Nodes 210, 214, 216, 218, and 220 correspond to the skip grams: "quick brown," "the quick," "fox jumped," "fox over," "the lazy," and "lazy dog" from the sentence "the quick brown fox jumped over the lazy dog." The parenthetical next to each word indicates the integer mapping corresponding to that word. To determine the start and ending word or words of the skip gram, server device 22 and/or client devices 100 may traverse the nodes of trie 200. Although each node in the example of FIG. 6 corresponds to a single word, any node may correspond to one or multiple words in other examples.

When server device 22 and/or client devices 100 initially determine whether to add nodes 210, 212, 214, 216, 218, and 220 to trie 200, server device 22 and/or client devices 100 determine whether a potential parent node exists for each candidate node. For example, if the word "brown" did not have a parent node because the parent node corresponding to "quick" (204) had been previously pruned, then node 210 corresponding to brown would not be added to trie. Server device 22 and/or client devices 100 may use the bloom filters associated with the nodes of the previous level (in this example, nodes 204, 206, and/or 208) to determine whether the candidate node to be added to the trie can be a child node of a parent node. The determination of whether to add a new node based on membership in a parent node's skip gram may be referred to as a "dynamic iceberg filter."

Additionally, it should be noted that the skip grams of trie 200 may be order-independent, such that a skip gram corresponding to "quick brown fox" is equivalent to "brown quick fox" or "fox quick brown," or any other permutation. To efficiently achieve order independence, server device 22 and/or client devices 100 may sort the nodes of trie 200 before performing lookup or storage of a node in trie 200. By sorting the trie and having order independence, memory usage associated trie 200 may be reduced, which may improve performance.

When determining whether to add a particular word to trie 200, server device 22 and/or client devices 100 perform a pruning step. During the pruning step, server device 22 and/or client devices 100 examine nodes of the previous level of the trie for possible removal. More particularly, codes from each node's "code histogram" are dropped if the number of times the count occurs is below the minimum count threshold needed for a rule. If, after the low count codes are filtered, the code histogram is empty, then that node is removed.

Server device 22 and/or client devices 100 may also prune nodes based on the number of enterprises associated with a node. If a node is associated with only a single hospital or enterprise, it may be more likely that it may be a result of a templated document, and thus the potential rule may be less useful than a rule than one that has evidence from multiple hospitals. Thus, if the number of enterprises associated with a particular node of the trie is too low, server device 22 and/or client devices 100 may prune that node.

In the example of FIG. 6, nodes 212, 216, and 218, and 220 all have parent nodes and are initially added to trie 200. However, the histogram counts associated with these nodes may be too low, and therefore server device 22 and/or client devices 100 may prune these nodes, which are indicated with a dashed border. Alternatively, the number of enterpriseIds associated with nodes 212, 216, and 218 may be too small, and thus server device 22 and/or client devices 100 may prune these nodes.

For nodes being added to level 2 of the trie, and further levels of depth, server device 22 and/or client devices 100 perform dynamic, on-the-fly filtering bloom filters. More particularly, when a new level of trie 200 is being built from the second level of depth and beyond, each of the possible codes from the unigram node are tested for "possible membership" in the parent's bloom filter. Server device 22 and/or client devices 100 only create child nodes if at least one code is judged possible. Using bloom filters may avoid the creation of unnecessary nodes that would be pruned later.

FIG. 7 is a conceptual diagram illustrating trie 200 after performing pruning. In FIG. 7, nodes 212, 216, and 218 have been pruned from trie 220. Because nodes 210, 214, and 220 have survived pruning, server device 22 and/or client devices 100 determine whether rules should be output based on the skip grams of nodes 210, 214, and 220.

More particularly, to determine whether a skip gram should be output as a rule, server device 22 and/or client devices 100 may calculate pointwise mutual information. In some examples, server device 22 and/or client devices 100 may calculate the pointwise mutual information according to the formula:

$$\log(\text{probability\_of\_code\_and\_feature\_set}/$$
$$(\text{probability\_of\_code}*\text{probability\_of\_feature\_set}).$$

The "probability_of_code" is the score or percent probability that a particular code appears in the medical documentation. The "probability_of_feature_set" is the score or percent probability that the feature set of a skip gram occurs in the medical documentation. The pointwise mutual information may be constructed from a node's count, the node's code histogram, and the global code histogram. If server device 22 and/or client devices 100 determine that a specified output threshold is equaled or exceeded, the rule, consisting of the skip gram set of features mapping to a specified code, server device 22 and/or client devices 100 may output the rule, e.g. to coding rules 74.

After server device 22 and/or client devices 100 output any rules, server device 22 and/or client devices 100 generate bloom filters for each of nodes 210, 214, and 220. After generating the bloom filter, server device 22 and/or client devices 100 remove each of the histograms associated with each of the nodes. Removing the histograms associated with each of the nodes may improve memory efficiency.

Server device 22 and/or client devices 100 perform each of the above steps (population, pruning, rule output, and bloom filter generation and histogram removal) using a distributed computing framework. However, in some examples, server 22 (e.g., a master spark node or another master node of a distributed computing framework) may perform the pruning, rule generation, bloom filter generation, and histogram removal steps. Additionally, the pruning, rule generation, bloom filter generation, and histogram removal steps may be executed in a single thread (as opposed to using multi-threading). As such, these steps may represent a performance bottleneck. Therefore, ensuring that the trie is represented in a memory-efficient manner is extremely important.

In various examples, the min_count parameter, as well as other configuration parameters that control parameters may be adjusted (e.g., by a user or automatically) to tune performance. For example, a low pointwise mutual information threshold might be applied to the pruning step to eliminate codes used in the dynamic iceberg filtering step.

Figure 8:
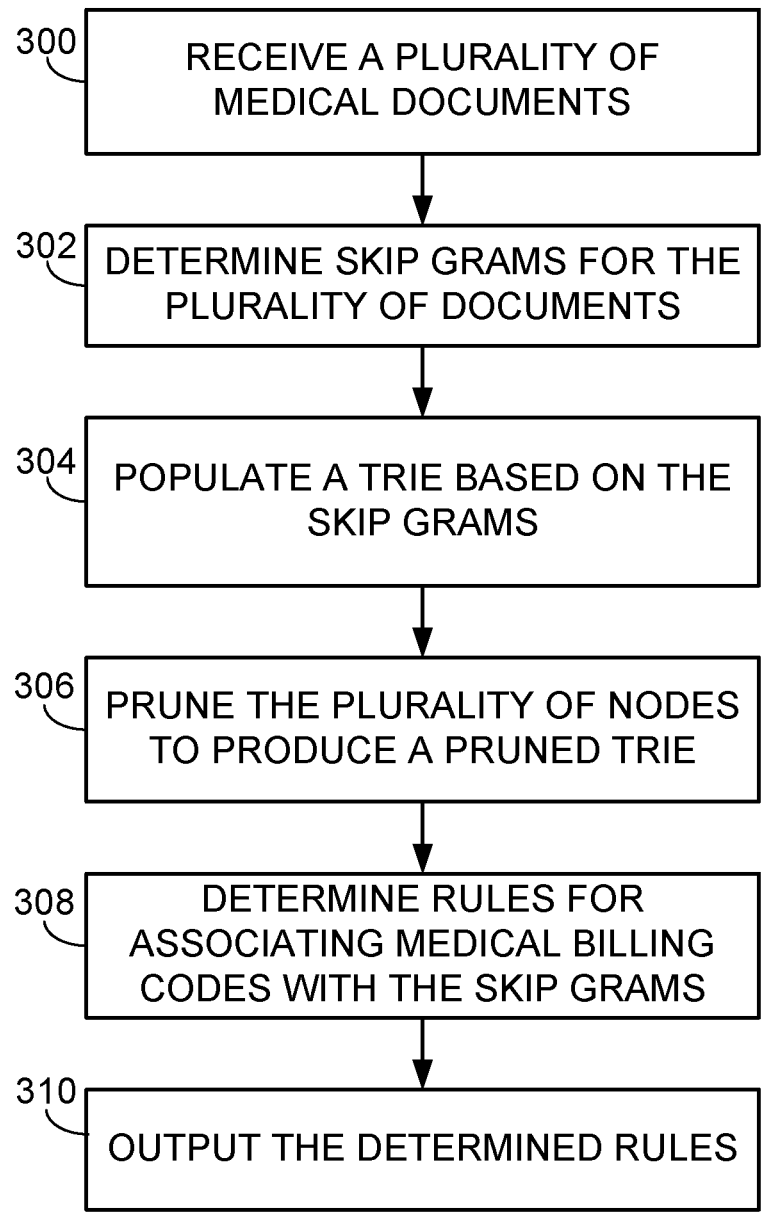
FIG. 8 is a flow diagram illustrating an example process for populating a trie and outputting medical coding rules in accordance with the techniques of this disclosure.

FIG. 8 is a flow diagram illustrating an example process for populating a trie and outputting medical coding rules in accordance with the techniques of this disclosure. FIG. 8 will be described from the perspective of sever 22 and client devices 100 of FIGS. 1 and 2, although any other computing devices or systems, or any combination thereof, may be used in other examples.

As shown in FIG. 8, processor 50 or processor 110 may be configured to receive receiving a plurality of medical documents (e.g., from repository 24) (300). Processor 50 and/or processor 110 may then determine skip grams comprising tokens for the plurality of medical documents (302), wherein each of the skip grams comprises one or more tokens of at least one of the medical documents, and populate the trie data structure based on the skip grams (304).

To populate the trie, processor 50 and/or processor 110 of server computing device 22 and client computing devices 100 may be further configured to add a null root node to the trie; and add a plurality of nodes to the trie, wherein the plurality of nodes each have a parent node comprising either: the root node or another one of the plurality of nodes, wherein each of the plurality of nodes comprises one of the determined skip grams, wherein, for every one of the plurality of nodes having a respective parent node, a skip gram of the one of the plurality of nodes has a greater size than a skip gram of the parent node of the one of the plurality of nodes.

Processor 50 and/or processor 110 may be further configured to prune the plurality of nodes of the trie based on one or more criteria to produce a pruned trie of nodes (306), determine rules for associating medical billing codes with the skip grams of the pruned trie of nodes based on pointwise mutual information (308), and output the determined rules (310). For example, processor 50 and/or processor 110 may be configured to prune the nodes of the trie based on one or more criteria such as integers, histograms, or other characteristics of the nodes. For example, processor 50 and/or processor 110 may use a threshold count for the histogram of each code as criteria such that, for example, a code may be dropped from a node if the count of the node's histogram is below a threshold number. The node may be entirely removed from the count if the count is zero. As another example, processor 50 and/or processor 110 may use a number of enterprises associated with each node as criteria such that, for example, a node associated with fewer enterprises (e.g., only a single hospital) is removed because the node may be the result of a template at that specific enterprise and less useful than a node arising from multiple enterprises. Processor 50 may output the determined rules to be stored as at least part of coding rules 74 and/or for review by a coding professional, as some examples. Processor 50 may execute training module 68 to perform these processes, and processor 110 may execute training module 132 to perform these processes.

The techniques of this disclosure may be implemented in a wide variety of computer devices, such as one or more servers, laptop computers, desktop computers, notebook computers, tablet computers, hand-held computers, smart phones, or any combination thereof. Any components, modules or units have been described to emphasize functional aspects and do not necessarily require realization by one or more different hardware units.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A server, client computing device, or any other computing device may also contain a more portable removable memory type to enable easy data transfer or offline data analysis.

The techniques described in this disclosure, including those attributed to server 22, repository 24, and/or computing device 100, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, remote servers, remote client devices, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. For example, any of the techniques or processes described herein may be performed within one device or at least partially distributed amongst two or more devices, such as between server 22 and/or client computing devices 100. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described herein. Any combination of the described operations or functions is contemplated. These and other examples are within the scope of the following claims.

What is claimed is:

1. A computer-implemented method for managing medical information, the method performed by one or more processors of at least one computing device, the method comprising:
   receiving, by the one or more processors, a plurality of medical documents;
   determining, by the one or more processors, skip grams comprising tokens for the plurality of medical documents, wherein each of the skip grams comprises one or more tokens of at least one of the medical documents;
   populating, by the one or more processors, a trie data structure based on the skip grams, wherein populating the trie comprises:
      adding a null root node to the trie; and
      adding a plurality of nodes to the trie,
      wherein the plurality of nodes each have a parent node comprising either: the null root node or another one of the plurality of nodes,
      wherein each of the plurality of nodes comprises one of the determined skip grams,
      wherein, for every one of the plurality of nodes having a respective parent node, a skip gram of the one of the plurality of nodes has a greater size than a skip gram of the parent node of the one of the plurality of nodes, wherein size is related to the number of words that a skip gram can span;
   pruning, by the one or more processors, the plurality of nodes of the trie based on one or more criteria to produce a pruned trie of nodes;
   determining, by the one or more processors, rules for associating medical billing codes with the skip grams of the pruned trie of nodes based on pointwise mutual information; and
   outputting, by the one or more processors, the determined rules.

2. The method of claim 1, wherein determining the skip grams comprises:
   generating a histogram that indicates frequencies of each of the words of the medical documents;
   producing an updated histogram comprising:
      removing, from the histogram, words of the medical documents that occur fewer than a minimum number of times in the medical documents based on the frequencies of the words; and
      determining the skip grams based on the updated histogram.

3. The method of claim 2, wherein producing the updated histogram further comprises:
   removing, from the histogram, words of each of the medical documents that occur in greater than a threshold percentage of the medical documents.

4. The method of claim 1, further comprising: mapping the tokens of the medical documents to unique integer representations of the tokens; and representing the skip grams of the plurality of nodes using the integer representations of the tokens.

5. The method of claim 1, further comprising:
   detecting sentence boundaries within the medical documents; and
   ignoring skip grams that span across the sentence boundaries.

6. The method of claim 1, further comprising:
   determining a bloom filter for the given one of the plurality of nodes, wherein the bloom filter indicates whether a candidate skip gram is not a member of the skip gram of the one of the plurality of nodes;
   responsive to determining that the candidate skip gram is not a member of the skip gram of the one of the plurality of nodes,
   removing a node associated with the candidate skip gram from the trie.

7. The method of claim 6, wherein the given one of the plurality of nodes is associated with a histogram, the method further comprising:
   removing the histogram responsive to determining the bloom filter for the given one of the plurality of nodes.

8. The method of claim 1, wherein each of the plurality of nodes is associated with one or more healthcare enterprise identifiers, wherein pruning the plurality of nodes further comprises pruning nodes of the plurality of nodes having less than a threshold number of the healthcare enterprise identifiers.

9. The method of claim 1, wherein determining the pointwise mutual information is based on a probability of both a medical code and feature set occurring, a probability of a medical code occurring, and a probability of the feature set occurring.

10. The method of claim 9,
    wherein determining the pointwise mutual information further comprises:
    log (probability_of_code_and_feature_set/(probabilty_of_code X probabilty_of_feature_set)),
    wherein probability_of_code_and_feature_set corresponds to the probability of both the medical code and feature set occurring,
    probability_of_code corresponds to the probability of a medical code occurring, and
    probability_of_feature_set corresponds to the probability of the feature set occurring.

11. A computerized system for managing medical information, the system comprising:
    one or more processors of at least one computing device, wherein the one or more processors are configured to:
      receive a plurality of medical documents;
      determine skip grams comprising tokens for the plurality of medical documents, wherein each of the skip grams comprises one or more tokens of at least one of the medical documents;
      populate a trie data structure based on the skip grams, wherein to populate the trie, the at least one computing device is further configured to:
        add a null root node to the trie; and
        add a plurality of nodes to the trie,
        wherein the plurality of nodes each have a parent node comprising either: the null root node or another one of the plurality of nodes,
        wherein each of the plurality of nodes comprises one of the determined skip grams,
        wherein, for every one of the plurality of nodes having a respective parent node, a skip gram of the one of the plurality of nodes has a greater size than a skip gram of the parent node of the one of the plurality of nodes, wherein size is related to the number of words that a skip gram can span;

prune the plurality of nodes of the trie based on one or more criteria to produce a pruned trie of nodes;

determine rules for associating medical billing codes with the skip grams of the pruned trie of nodes based on pointwise mutual information; and output the determined rules.

12. The system of claim 11, wherein to determine the skip gram, the one or more processors are configured to:

generate a histogram that indicates frequencies of each of the words of the medical documents;

produce an updated histogram comprising:

remove, from the histogram, words of the medical documents that occur fewer than a minimum number of times in the medical documents based on the frequencies of the words; and determine the skip grams based on the updated histogram.

13. The system of claim 12, wherein to produce the updated histogram, the one or more processors are further configured to:

removing, from the histogram, words of each of the medical documents that occur in greater than a threshold percentage of the medical documents.

14. The system of claim 11, wherein the one or more processors are further configured to:

map the tokens of the medical documents to unique integer representations of the tokens; and represent the skip grams of the plurality of nodes using the integer representations of the tokens.

15. The system of claim 11, wherein the one or more processors are further configured to:

detect sentence boundaries within the medical documents; and ignore skip grams that span across the sentence boundaries.

16. The system of claim 11, wherein the one or more processors are further configured to:

determine a bloom filter for the given one of the plurality of nodes, wherein the bloom filter indicates whether a candidate skip gram is not a member of the skip gram of the one of the plurality of nodes;

responsive to determining that the candidate skip gram is not a member of the skip gram of the one of the plurality of nodes; and remove a node associated with the candidate skip gram from the trie.

17. The system of claim 16, wherein the given one of the plurality of nodes is associated with a histogram, the one or more processors are further configured to:

remove the histogram responsive to determining the bloom filter for the given one of the plurality of nodes.

18. The system of claim 11, wherein each of the plurality of nodes is associated with one or more healthcare enterprise identifiers, wherein to prune the plurality of nodes, the at least one computing device is further configured to prune nodes of the plurality of nodes having less than a threshold number of the healthcare enterprise identifiers.

19. The system of claim 11, wherein determining the pointwise mutual information is based on a probability of both a medical code and feature set occurring, a probability of a medical code occurring, and a probability of the feature set occurring.

20. The system of claim 19, wherein to determine the pointwise mutual information, the one or more processors are further configured to calculate:

log (probability_of_code_and_feature_set/(probabilty_of_code X probabilty_of_feature_set)), wherein probability_of_code_and_feature_set corresponds to the probability of both the medical code and feature set occurring, probability_of_code corresponds to the probability of the medical code occurring, and probability_of_feature_set corresponds to the probability of the feature set occurring.

21. A non-transitory computer-readable storage medium comprising instructions that, when executed, cause one or more processors to:

receive a plurality of medical documents;

determine skip grams comprising tokens for the plurality of medical documents, wherein each of the skip grams comprises one or more tokens of at least one of the medical documents;

populate a trie data structure based on the skip grams, wherein the instructions that cause the at least one processor to populate the trie further comprise instructions that cause the at least one processor to:

add a null root node to the trie; and add a plurality of nodes to the trie, wherein the plurality of nodes each have a parent node comprising either: the null root node or another one of the plurality of nodes, wherein each of the plurality of nodes comprises one of the determined skip grams, wherein, for every one of the plurality of nodes having a respective parent node, a skip gram of the one of the plurality of nodes has a greater size than a skip gram of the parent node of the one of the plurality of nodes, wherein size is related to the number of words that a skip gram can span;

prune the plurality of nodes of the trie based on one or more criteria to produce a pruned trie of nodes;

determine rules for associating medical billing codes with the skip grams of the pruned trie of nodes based on pointwise mutual information; and output the determined rules.

* * * * *

UNITED STATES PATENT AND TRADEMARK OFFICE
CERTIFICATE OF CORRECTION

Page 1 of 2

PATENT NO. : 10,565,351 B2
APPLICATION NO. : 15/242670
DATED : February 18, 2020
INVENTOR(S) : Nossal et al.

It is certified that error appears in the above-identified patent and that said Letters Patent is hereby corrected as shown below:

On the Title Page

<u>Column 2, (Other Publications)</u>
Line 2  Delete "Corrrection" and insert -- Correction --, therefor.

In the Specification

<u>Column 4</u>
Line 2  Delete ""# xzy123")" and insert -- "#xzy123") --, therefor.

<u>Column 5</u>
Line 5  Delete "lincrements," and insert -- 1 increments, --, therefor.

<u>Column 14</u>
Line 37  Delete ""the token"" and insert -- "the_token" --, therefor.
Lines 37-38  Delete ""the token" and insert -- "the_token --, therefor.
Line 40  Delete "The token" and insert -- The_token --, therefor.
Line 43  Delete ""the token" and insert -- "the_token --, therefor.
Line 60  Delete "bloomfilter" and insert -- bloom filter --, therefor.

<u>Column 15</u>
Line 43  Delete "operatation)." and insert -- operation). --, therefor.

In the Claims

<u>Column 22</u>
Lines 37-38  In Claim 10, delete "(probabilty" and insert -- (probability --, therefor.
Line 38  In Claim 10, delete "probabilty" and insert -- probability --, therefor.

Signed and Sealed this
Twenty-fifth Day of August, 2020

Andrei Iancu
*Director of the United States Patent and Trademark Office*

CERTIFICATE OF CORRECTION (continued)
U.S. Pat. No. 10,565,351 B2

Column 24
Lines 15-16    In Claim 20, delete "(probabilty" and insert -- (probability --, therefor.
Line 16        In Claim 20, delete "probabilty" and insert -- probability --, therefor.